United States Patent [19]

Montorsi et al.

[11] 4,007,220

[45] Feb. 8, 1977

[54] PREPARATION OF PHTHALALDEHYDIC ACID FROM $\alpha,\alpha,\alpha,\alpha',\alpha'$-PENTACHLORO-O-XYLENE

[75] Inventors: Giorgio Montorsi, Milan; Renato Pellizzato, Varese; Anacleto Gianantonio, Milan, all of Italy

[73] Assignee: Gruppo Lepetit S.p.A., Milan, Italy

[22] Filed: Aug. 13, 1975

[21] Appl. No.: 604,293

[30] Foreign Application Priority Data

Sept. 20, 1974 United Kingdom ............ 40984/74

[52] U.S. Cl. ...................... 260/515 R; 260/250 R
[51] Int. Cl.² ...................................... C07C 63/04
[58] Field of Search ................................ 260/515 R

[56] References Cited

UNITED STATES PATENTS

| 2,748,161 | 5/1956 | Head et al. | 260/515 R |
| 2,748,162 | 5/1956 | Head et al. | 260/515 R |
| 3,624,157 | 11/1971 | Inqwalson et al. | 260/515 R |

Primary Examiner—Bernard Helfin
Assistant Examiner—G. Breitenstein
Attorney, Agent, or Firm—Theodore Post; C. Kenneth Bjork

[57] ABSTRACT

High yields of phthalaldehydic acid from $\alpha,\alpha,\alpha,\alpha',\alpha'$-pentachloro-o-xylene can be obtained in an excellent degree of purity if a mixture of said pentachloroxylene and phthalaldehydic acid in water is heated to a temperature between about 80° and about 180° C., and preferably at the boiling temperature of the reaction mixture. The mutual ratio of the reactants is not critical, and may vary within wide ranges, although it is usually preferred to have such a ratio between the said pentachloroxylene and phthalaldehydic acid that for each part by weight of the former at least 0.1 part by weight of the latter is present. Practically, there is no upper limit to the amount of phthalaldehydic acid which may be present, even to a large molecular excess.

4 Claims, No Drawings

...

PREPARATION OF PHTHALALDEHYDIC ACID FROM $\alpha,\alpha,\alpha',\alpha'$-PENTACHLORO-O-XYLENE

BACKGROUND OF THE INVENTION

Hydrolysis in water or in aqueous hydrochloric acid of $\alpha,\alpha,\alpha\alpha',\alpha'$-pentachloro-o-xylene to prepare phthalaldehydic acid proceeds very slowly and requires several days. Alkaline hydrolysis is not suitable because of the presence of an aldehydic group in the desired reaction product, which would then undergo more or less extensive polymerization with concomitant formation of condensation by-products and colored substances difficult to eliminate.

The hydrolysis rate is considerably increased by the use of a catalyst. For instance, U.S. Pat. No. 2,748,161 describes a process of catalytic hydrolysis of pentachloroxylene in the presence of an aromatic sulfonic acid selected from sulfonated aromatic hydrocarbons of the benzene and naphthalene series and the sulfonated nuclear-halogenated derivatives thereof, at 90°–120° C. On the other hand, U.S. Pat. No. 2,748,162 describes the hydrolysis of pentachloroxylene in aqueous hydrohalic acid and in the presence of at least one metal halide selected from zinc chloride, zinc bromide, ferric chloride, ferric bromide, cadmium chloride and cadmium bromide at 100°–150° C. These processes give acceptable yields of phthalaldehydic acid, but the presence of large amounts of the employed catalyst in the reaction mixture creates severe technical difficulties of separation, particularly when the manufacture is carried out on an industrial scale. Moreover, the presence of metallic ions, such as $Zn^{2+}$, $Fe^{3+}$ and $Cd^{2+}$, ions in the waste creates serious ecological problems.

On the other hand, the absence of impurities from phthalaldehydic acid is essential if it is to be used in organic light-sensitive compositions, such as those described in British Pat. No. 1,170,265 or in French Pat. No. 2,016,397. A high-purity standard is also of extreme importance if phthalaldehydic acid is to be employed as the starting material for manufacturing 1(2H)-phthalazinone, a substance of high commercial utility both as a component of light-sensitive compositions, such as those described in U.S. Pat. No. 3,682,684 and in German Pat. Nos. 1,908,758, 2,042,054 and 2,139,252, and as an intermediate for a number of organic substances of much use in all fields of technology. Thus, if phthalaldehydic acid is reacted with hydrazine to prepare 1(2H)-phthalazinone, or with hydrazine derivatives such as semicarbazide or thiosemicarbazide, the presence of trace amounts of metals in the starting phthalaldehydic acid may catalyze the decomposition of those reactants, in some instances accompanied by explosions. As a matter of fact, heavy metals in the form of their salts and oxides, particularly ferric, cupric, molybdic and chromic ions, are known to favor catalytically that decomposition; see J. E. Troyan, "Properties, Production and Uses of Hydrazine", Industrial Engineering Chemistry, 45, 2608 (1953).

SUMMARY OF THE INVENTION

It has now been discovered that high yields of phthalaldehydic acid from $\alpha,\alpha,\alpha,\alpha',\alpha'$-pentachloro-o-xylene can be obtained in an excellent degree of purity if a mixture of said pentachloroxylene and phthalaldehydic acid in water is heated to a temperature between about 80° and 180° C., and preferably at the boiling temperature of the reaction mixture. The mutual ratio of the reactants is not critical and may vary within wide limits, although it is usually preferred to have such a ratio between said pentachloroxylene and phthalaldehydic acid that for each part by weight of the former at least 0.1 part by weight of the latter is present. Practically, there is no upper limit to the amount of phthalaldehydic acid which may be present, even to large molecular excesses.

The amount of water in the reaction medium may be regulated according to the total amount of the two reactants present in the reaction mass, provided the stoichiometric amount necessary for the hydrolysis of said pentachloroxylene is present. The reaction proceeds smoothly with evolution of hydrogen chloride and is obviously terminated as soon as this evolution subsides. At the end of the reaction, the mass is diluted with water and cooled, and the insoluble portion is collected and thoroughly washed to eliminate chloride ions. The product crystals of phthalaldehydic acid are recovered in a state of high purity and in yields ranging from 90 to 100 percent.

Due to the easy reaction course, the manufacture of phthalaldehydic acid may be carried out in a continuous manner, for example in a series of mutually connected reaction vessels, according to the usual technologies for continuous operations, which may offer advantages of time and cost, particularly when working on a large scale.

For practical purposes, the said pentachloroxylene and phthalaldehydic acid are mixed together in one of the above-indicated proportions, and water is added in an amount as indicated above, to provide at least the stoichiometric amount necessary for hydrolyzing the said pentachloroxylene present. The reaction mass is then heated to 80°–180° C., preferably at the boiling temperature of the mixture at atmospheric pressure. Hydrogen chloride is formed in the reaction and accumulates in the mixture until it is saturated. To speed up the reaction rate, it is convenient to avoid excessive concentrations of hydrogen chloride, which is vented from the reaction zone. On the other hand, if a temperature higher than the boiling temperature of the mixture is employed, it will be necessary to work in a pressure vessel such as an autoclave. The hydrolysis is complete when hydrogen chloride evolution subsides, and this happens usually after about 5 to about 20 hours, depending on the selected conditions of temperature, pressure and mutual ratio of the two reactants and water.

DESCRIPTION OF SOME PREFERRED EMBODIMENTS

The following additional description and examples further describe the invention and the manner and process of making and using it to enable the art skilled to make and use the same and set forth the best mode contemplated by the inventors of carrying out the invention.

EXAMPLE 1

A mixture of 70 g. of $\alpha,\alpha,\alpha,\alpha',\alpha'$-pentachloro-o-xylene, 50 g. of phthalaldehydic acid and 70 g. of water is refluxed with stirring for 10 hours, after which time the evolution of hydrogen chloride subsides. About one hundred milliliters of boiling water is added gradually with stirring and the mixture is cooled. After settling, the solids are collected and carefully washed with water. After drying, 86 g. of pure phthalaldehydic acid is obtained, m.p. 97°–98° C. The yield calculated on the starting pentachloroxylene is 95 percent.

If the reaction is carried out under the same conditions, but in the absence of phthalaldehydic acid, not less than two days of heating at reflux is needed to obtain comparable results.

EXAMPLE 2

By operating exactly as in Example 1, but using 70 g. of the said pentachloroxylene, 70 g. of phthalaldehydic acid and 40 g. of water, the hydrolysis is complete after about 8 hours. Yield 105 g. (92 percent) of pure phthalaldehydic acid.

EXAMPLE 3

This is an example of a continuous operation in carrying out the process of the invention.

Two hundred grams/hour of molten $\alpha,\alpha,\alpha,\alpha',\alpha'$-pentachloro-o-xylene and 85 grams/hours of water are fed continuously into the first of a series of four reaction vessels each having a volume of 1 liter and containing a 70 percent aqueous solution of phthalaldehydic acid heated to reflux. The mass coming out from the first reaction vessel passes continuously into the second reaction vessel, and so on. The hydrogen chloride which forms is vented and collected in water. Once the fourth reaction vessel has reached operative conditions, a product is continuously discharged from it which, after dilution 1:1 with hot water and cooling, is collected and dried, giving 104 grams/hour of phthalaldehydic acid. The yield is 96 percent.

We claim:
1. A process for preparing phthalaldehydic acid having the formula

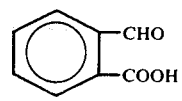

by heating at a temperature between about 80° and about 180° C a mixture of $\alpha,\alpha,\alpha,\alpha',\alpha'$-pentachloro-o-xylene and at least 0.1 part by weight of phthalaldehydic acid per part by weight of said pentachloroxylene as the sole catalyst in at least the stoichiometric amount of water necessary to hydrolyze said pentachloroxylene for a time sufficient to hydrolyze said pentachloroxylene to phthalaldehydic acid.

2. The process of claim 1 wherein the reaction mixture is heated to its boiling temperature at atmospheric pressure.

3. The process of claim 1 wherein the hydrogen chloride which forms during the reaction is vented as formed from the reaction zone.

4. The process of claim 1 wherein molten $\alpha,\alpha,\alpha,\alpha',\alpha'$-pentachloro-o-xylene and water are fed continuously into a series of reaction vessels each containing an aqueous solution of phthalaldehydic acid maintained at reflux temperature, venting by-product hydrogen chloride as formed, diluting product from the terminal reaction vessel with water, cooling the resulting product and collecting and drying product phthalaldehydic acid.

* * * * *

UNITED STATES PATENT AND TRADEMARK OFFICE
CERTIFICATE OF CORRECTION

PATENT NO. : 4,007,220
DATED : February 8, 1977
INVENTOR(S) : Giorgio Montorsi et al.

It is certified that error appears in the above—identified patent and that said Letters Patent are hereby corrected as shown below:

Column 1, line 7, "$\alpha,\alpha,\alpha\alpha',\alpha'$-pentachloro-o-xylene" should read --$\alpha,\alpha,\alpha,\alpha',\alpha'$-pentachloro-o-xylene--.

Column 4, bridging lines 24 and 25 (Claim 4, bridging lines 1 and 2), "$\alpha,\alpha,\alpha,\alpha'\lambda,\alpha'$-pentachloro-o-xylene" should read --$\alpha,\alpha,\alpha,\alpha',\alpha'$-pentachloro-o-xylene--.

Signed and Sealed this

Fifteenth Day of November 1977

[SEAL]

Attest:

RUTH C. MASON
Attesting Officer

LUTRELLE F. PARKER
Acting Commissioner of Patents and Trademarks